(12) United States Patent
Yeh et al.

(10) Patent No.: US 12,226,212 B2
(45) Date of Patent: Feb. 18, 2025

(54) ANALYSIS APPARATUS, DIAGNOSTIC SYSTEM AND ANALYSIS METHOD FOR ADHD

(71) Applicant: National Central University, Taoyuan (TW)

(72) Inventors: Shih-Ching Yeh, Taoyuan (TW); Hsiao-Kuang Wu, Taoyuan (TW)

(73) Assignee: National Central University, Taoyuan (TW)

( * ) Notice: Subject to any disclaimer, the term of this patent is extended or adjusted under 35 U.S.C. 154(b) by 69 days.

(21) Appl. No.: 17/834,929

(22) Filed: Jun. 8, 2022

(65) Prior Publication Data
US 2024/0225504 A1 Jul. 11, 2024

(30) Foreign Application Priority Data
Apr. 13, 2022 (TW) .................................. 111114085

(51) Int. Cl.
*A61B 5/369* (2021.01)
*A61B 5/16* (2006.01)
*G06F 3/01* (2006.01)
*G16H 50/20* (2018.01)

(52) U.S. Cl.
CPC .............. *A61B 5/168* (2013.01); *A61B 5/163* (2017.08); *A61B 5/369* (2021.01); *G06F 3/012* (2013.01); *G06F 3/013* (2013.01); *G06F 3/015* (2013.01); *G16H 50/20* (2018.01)

(58) Field of Classification Search
CPC ......... A61B 5/168; A61B 5/163; A61B 5/369; G16H 50/20; G06F 3/012; G06F 3/015
See application file for complete search history.

(56) References Cited

FOREIGN PATENT DOCUMENTS

| CN | 113288171 A | 8/2021 |
|---|---|---|
| WO | WO 2018/132483 A1 | 7/2018 |
| WO | WO 2021/135692 A1 | 7/2021 |

*Primary Examiner* — Kesha Frisby
(74) *Attorney, Agent, or Firm* — TOMANAGEIP (57) ABSTRACT

An analysis apparatus for ADHD is suitable for receiving a plurality of sensing data from a subject. The analysis apparatus comprises a plurality of first stage processing units, a combinator, and a second stage processing unit. Each of the first stage processing units performs a first DNN processing for the sensing data respectively, such that a plurality of first learning results are generated. The first learning results are combined by the combinator into a combination data. The second stage processing unit performs a second DNN processing for the combination data to generate an analysis result.

14 Claims, 8 Drawing Sheets

ANALYSIS APPARATUS, DIAGNOSTIC SYSTEM AND ANALYSIS METHOD FOR ADHD

BACKGROUND OF THE INVENTION

1. Field of the Invention

The present disclosure relates to an analysis and diagnostic method for ADHD, and in particular to an analysis and diagnostic method for ADHD by deep neural networks (DNN).

2. Description of the Related Art

Attention deficit/hyperactivity disorder (ADHD) is a complex neurodevelopmental disorder that can affect sufferer's ability to function in many different aspects of his or her life, such as at school, at work, and even at home. ADHD, as its name implies that its comprising attention deficit and hyperactivity disorder primarily. Accordingly, there is a checklist to help us for the diagnostic of ADHD. The check list involves two main parts. One of the parts is for the evaluations of attention deficit, and another part is for evaluation of hyperactivity disorder.

The first part for evaluation of attention deficit involves 9 items, such like details often missed, easily distracted by stimuli, task avoidance, etc. The second part for evaluation of hyperactivity disorder also involves 9 items, such like going ono stop, impatience, restless, etc. Conventionally, if we need to evaluate, it usually spends long period and high cost of human power. In addition, the traditional matter of diagnostic for ADHD needs specific environment, such than it is limited by test environment.

BRIEF SUMMARY OF THE INVENTION

The present disclosure provides an analysis apparatus and method for ADHD, being able to analysis whether a test-receiver suffer ADHD securely without mistake from test-provider.

In addition, the present disclosure provides a diagnostic system for ADHD for determining whether a test-receiver has ADHD tendency without the effect of environment.

The analysis apparatus for ADHD provided by the present disclosure is suitable for receiving a plurality of sensing data from a test-receiver. The analysis apparatus comprises a plurality of $1^{st}$ stage processer, a combinator, and a $2^{nd}$ stage processor. Each of the $1^{st}$ stage processer is configured for preforming a $1^{st}$ stage DNN processing for one of received sensing data respectively and output a $1^{st}$ stage learning result. The combinator combines the $1^{st}$ stage learning results into a combination data. The $2^{nd}$ stage processer performs a $2^{nd}$ stage DNN processing for the combination data and generate an analysis result.

In some embodiments, the analysis apparatus further comprises a plurality of feature extractors for receiving the sensing data and extracting a plurality of feature values from the sensing data. Each of the feature extractors is coupled to one of $1^{st}$ stage processer respectively, such that the each of $1^{st}$ stage processers receives one of the feature values and performs $1^{st}$ stage DNN processing for the feature values.

In some embodiments, the sensing data comprising the test-receiver's EEG data, eye motion sensing data and at least one movement sensing data.

In addition, the diagnostic system provided by the present disclosure comprises an immersive module and an analysis module. The immersive module provides at least one of a test video and a test audio to a test-receiver, so as to sense the response for the test video and/or test audio from the test-receiver and output a plurality of sensing data. The sensing data transmitted to the analysis module through wire or wireless interface. The analysis module comprises a plurality of $1^{st}$ stage processer, a combinator, and a $2^{nd}$ stage processor. Each of the $1^{st}$ stage processer is configured for preforming a $1^{st}$ stage DNN processing for one of received sensing data respectively and output a $1^{st}$ stage learning result. The combinator combines the $1^{st}$ stage learning results into a combination data. The $2^{nd}$ stage processer performs a $2^{nd}$ stage DNN processing for the combination data and generate an analysis result.

In some embodiments, the analysis module further comprises a plurality of feature extractors for receiving the sensing data and extracting a plurality of feature values from the sensing data. Each of the feature extractors is coupled to one of $1^{st}$ stage processer respectively, such that the each of $1^{st}$ stage processers receives one of the feature values to perform $1^{st}$ stage DNN processing.

In some embodiments, the immersive module comprises a head mounted display (HMD) for displaying the test video and sensing the test-receiver's response to output at least one of sensing data. In perfectible, the HMD comprises a controller, a display unit, an eye motion tracker, a movement sensor and a transceiver. The controller is coupled to the display unit, eye motion tracker, movement sensor and transceiver. The eye motion tracker is configured to sense the motion of test-receiver's eyeball and output an eye motion sensing data. The movement sensor is configured to sense the movement of the test-receiver's head and output a head movement sensing data. When the transceiver receives the test video, the controller controls the display unit to display the test video. In addition, the controller controls the transceiver transmitting the eye motion sensing data and the head movement sensing data to the analysis module as at least part of the sensing data.

In other embodiments, the HMD further comprises an EEG sensor, which is configured to sense the test-receiver's brainwave and output an EEG sensing data. When the EEG sensor outputs the EEG sensing data, the controller controls the transceiver transmitting the EEG sensing data to the analysis module as at least part of the sensing data.

In other embodiments, the immersive module further at least one of handheld operator, which is coupled to the transceiver by wire or wireless matter. The handheld operator is able to sense the test-receiver's gesture and/or operation on the handheld operator and output an operation sensing data. The handheld operator transmits the operation sensing data to the transceiver as the plurality of sensing data transmitted to the analysis module.

In other embodiments, the diagnostic system further comprises a $1^{st}$ host and a $2^{nd}$ host. The $1^{st}$ host is coupled to the transceiver by wire or wireless matter. The $2^{nd}$ host has the analysis module and be coupled to the $1^{st}$ host by wire or wireless matter. The $1^{st}$ host is able to transmit the test video to the transceiver or receive the sensing data from the transceiver. The $1^{st}$ host transmits received sensing data to the $2^{nd}$ host, such that the analysis module is able to analysis the sensing data. In some embodiments, the $1^{st}$ host is coupled to the transceiver and/or $2^{nd}$ host by WiFi, mobile network, Bluetooth, ZigBee or other wireless communication protocol. In further embodiments, the $1^{st}$ host is coupled to the transceiver and/or the $2^{nd}$ host by USB, cable, fiber cable or other communication wire. The $1^{st}$ host and/or $2^{nd}$ is a desktop computer, a portable computer, an industry computer, a tablet, or a mobile communication device.

In some embodiments, the analysis system further comprises a host having the analysis module and being coupled to the transceiver by wire or wireless matter. The host is able to transmit the test video to the transceiver and receiver the sensing data from the transceiver, such that the analysis module installed in the host performs analysis for the sensing data. In some embodiments, the host is coupled to the transceiver by WiFi, mobile network, Bluetooth, ZigBee or other wireless communication protocol. In further embodiments, the host is coupled to the transceiver by USB, cable, fiber cable or other communication wire. Furthermore, the host is a desktop computer, a portable computer, an industry computer, a tablet, or a mobile communication device.

The analysis method provided by the present disclosure comprises the following steps: performing a $1^{st}$ DNN processing for each of sensing data respectively, so as to output a plurality of $1^{st}$ stage learning results; combining the $1^{st}$ stage learning results into a combination data; performing a $2^{nd}$ DNN processing for the combination data to output an analysis result for showing whether a test-receiver has ADHD tendency.

Since the present disclosure adopts DNN for analyzing the test-receiver's sensing data to determine whether the test-receiver has ADHD tendency, the present disclosure is able to avoid the mistake resulted by the objective determination. In addition, since the present disclosure adopts immersive module to provide the test video and/or test audio to the test-receiver, the present disclosure is not limited by the location or environment.

DETAILED DESCRIPTION OF THE INVENTION

To facilitate understanding of the object, characteristics and effects of this present disclosure, embodiments together with the attached drawings for the detailed description of the present disclosure are provided.

In the following paragraphs, A "couples to" B may means A directly or in-directly connecting to B, such like A connects to B by active or passive component. Furthermore, the meaning of "couple" may involve the analog electric signal or digital data exchanging through wire or wireless connection.

Figure 1:
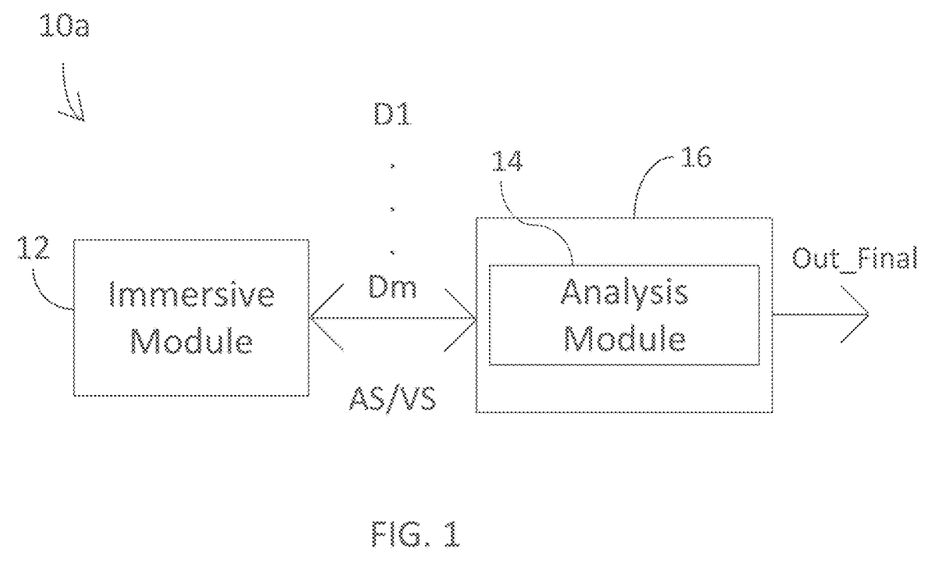
FIG. 1 is shown as a block diagram of a diagnostic system for ADHD according to one embodiment of the present disclosure.

FIG. 1 is shown a block diagram of a diagnostic system for ADHD according to one embodiment of the present disclosure. Please referring the FIG. 1, the diagnostic system 10*a* provided by the present embodiment comprises an immersive module 12 and an analysis module 14. The analysis module 14 is, for example, a programmable AI system and capable for being installed in a host device 16. In this embodiment or the embodiments hereafter, the host device means a machine having at least of central processing unit, display unit, and communication unit. In preferred embodiment, the host device 16 further has a storage unit and an input unit. The host device 16 is, for example but not limited as, a desktop computer, a portable computer, a specific industry computer, a tablet, a server, or a mobile communication device. In addition, the immersive module 12 is able to couple the host device 16 via wire or wireless matter. For example, the immersive module 12 is able to be coupled to the host device 16 via WiFi, mobile network, Bluetooth, ZigBee, or other wireless communication protocol. In other embodiments, the host device 16 is coupled to the immersive module 12 via USB, cable, fiber cable or other type of communication wire.

The host device 16 is able to transmit a test video VS and/or test audio AS to the immersive module 12, such that the immersive module 12 provides the test video VS and/or test audio AS to the test-receiver and generates a plurality of sensing data D1~Dm, wherein m is an integral greater than 1. The sensing data D1~Dm are capable for being transmitted to the analysis module 14, such that the analysis module 14 is able to analyze the sensing data and generate an analysis result Out_Final, which presents whether the test-receiver has the tendency with ADHD. For example, the analysis module 14 can output a percentage value to show the level of the test-receiver suffering with ADHD.

Figure 2:
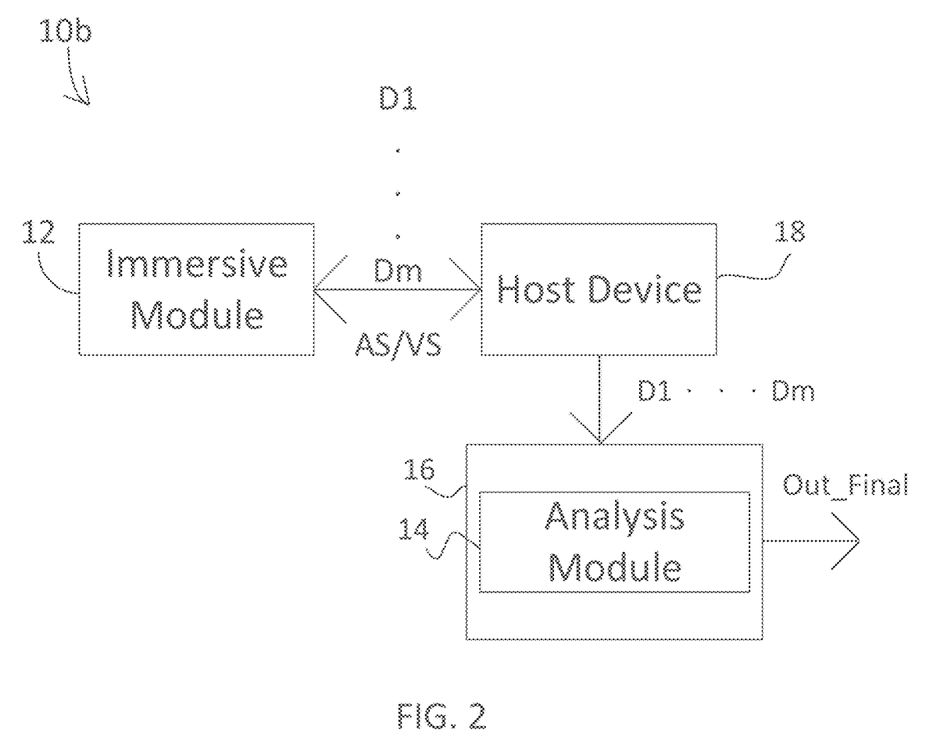
FIG. 2 is shown as a block diagram of a diagnostic system for ADHD according to another embodiment of the present disclosure.

FIG. 2 is shown as a block diagram of a diagnostic system for ADHD according to another embodiment of the present disclosure. Please referring to FIG. 2, the diagnostic system 10*b* provided by the present embodiment further comprises another host device 18 compared to the diagnostic system 10*a*. The host device 18 is able to couple with the immersive module 12 and/or host device 16 via wire or wireless matter. For example, the host device 18 is able to couple with immersive module 12 and/or host device 16 via WiFi, mobile network, Bluetooth, ZigBee or other wireless communication protocol. In other embodiments, the host device 18 is able to couple with the immersive module 12 and/or hot device 16 via USB, cable, fiber cable or other type of communication wire. In this embodiments, the host device 18 is, for example but not limited as, a desktop computer, a portable computer, a specific industry computer, a tablet, a server, or a mobile communication device.

The host device 18 is capable for transmitting the test video VS and/or test audio AS to the immersive module 12, and receiving the sensing data D1~Dm from the immersive module 12. When the host device 18 receives the sensing data D1~Dm, the sensing data D1~Dm are transmitted to the host device 16, such that the host device 16 with the analysis module 14 analyzes the sensing data D1~Dm.

Figure 3A:
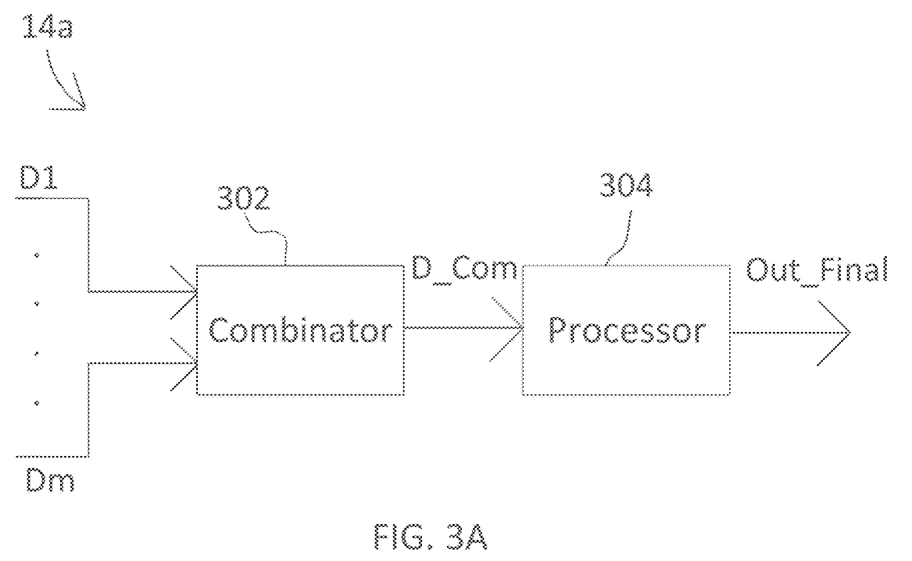
FIG. 3A is shown as a block of analysis module according to the first embodiment of the present disclosure.

FIG. 3A is shown as a block of analysis module according to the first embodiment of the present disclosure. Please referring to the FIG. 3A, the analysis module 14a provided by the present embodiment comprises a combinator 302 and processor 304. The combinator combines received sensing data D1~Dm into a combination data D_Com. In addition, the processor 304 couples with the combinator 302, so as to perform a DNN processing for the combination data D_Com and generate the analysis result Out_Final.

Figure 3B:
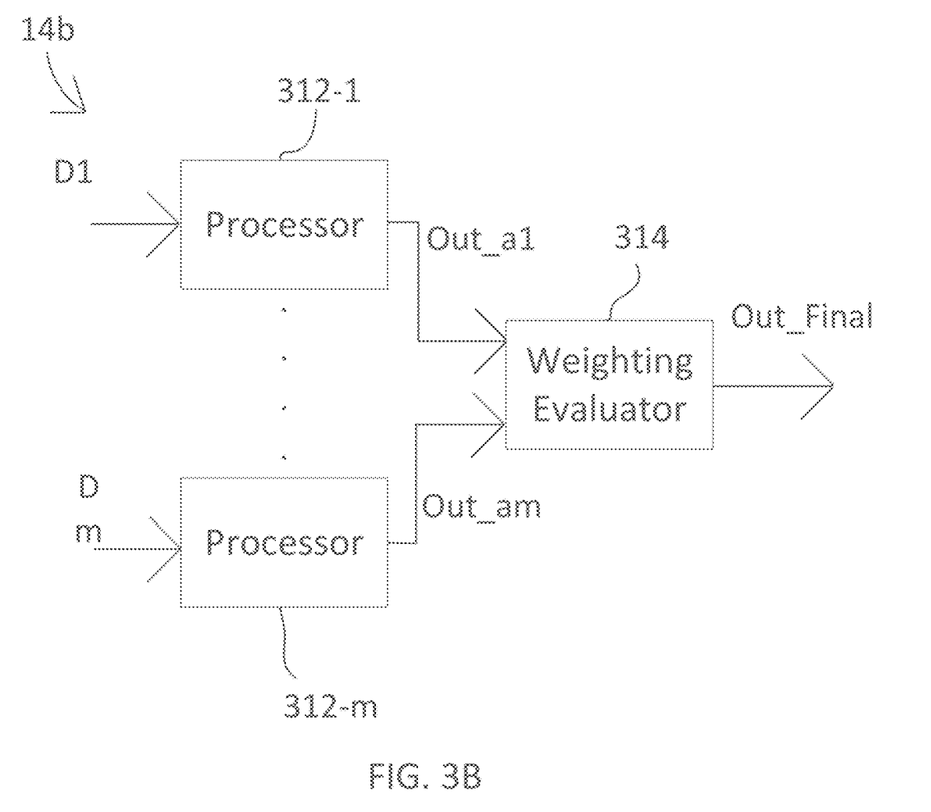
FIG. 3B is shown as a block of analysis module according to the second embodiment of the present disclosure.

FIG. 3B is shown as a block of analysis module according to the second embodiment of the present disclosure. Please referring to the FIG. 3B, the analysis module 14b provided by the present embodiment comprises a plurality of processors 312-1~312-m and a weighting evaluator 314. Each of the processors 312-1~312-m performs the DNN process for one of the sensing data D1~Dm respectively, and generates a learning result Out_a1~Out_am. In addition, the weighting evaluator 314 couples with the processors 312-1~312-m, so as to perform a weighting calculation for the learning result Out_a1~Out_am and obtain the analysis result Out_Final.

Figure 3C:
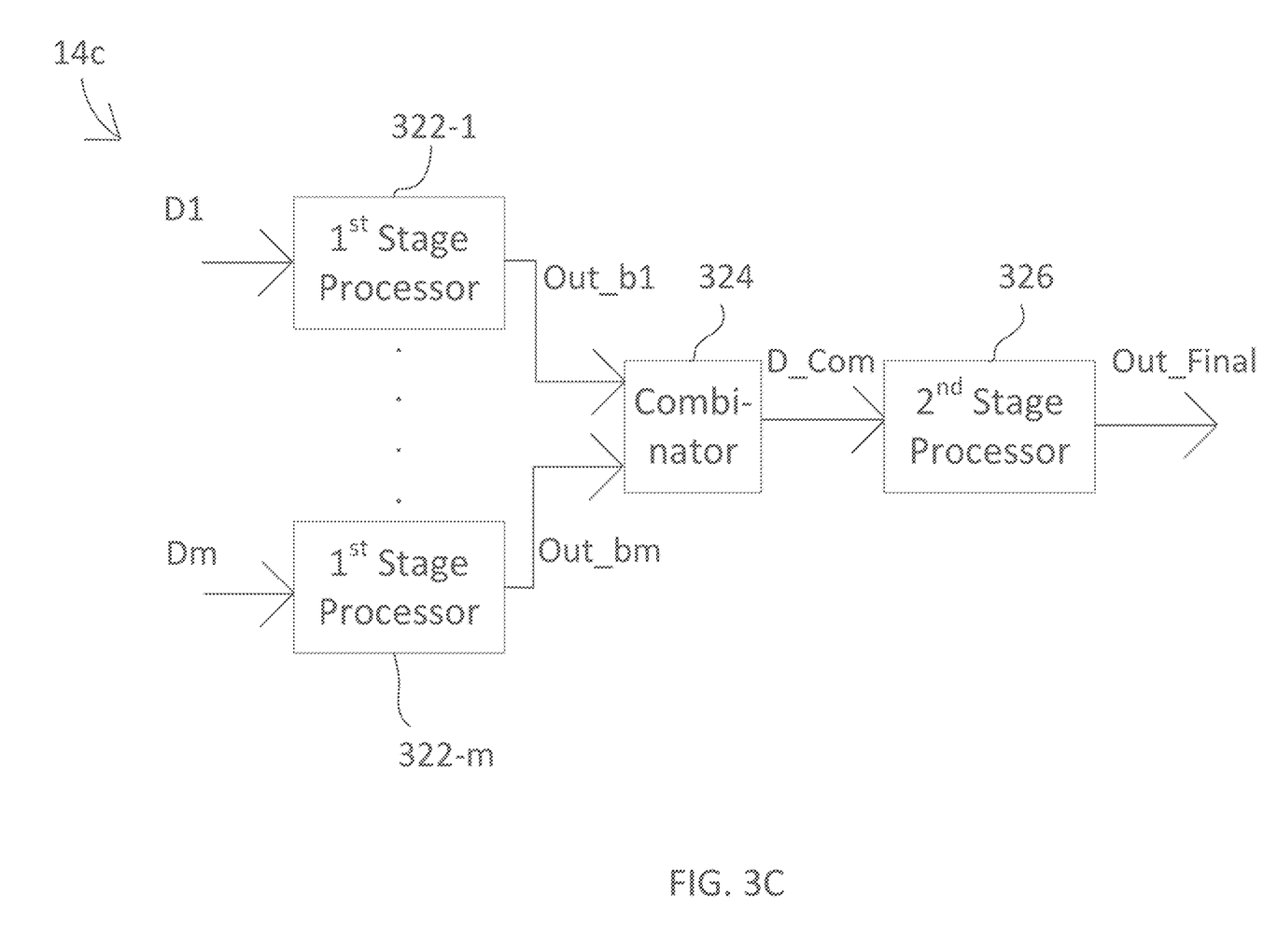
FIG. 3C is shown as a block of analysis module according to the third embodiment of the present disclosure.

FIG. 3C is shown as a block of analysis module according to the third embodiment of the present disclosure. Please referring to FIG. 3C, the analysis module 14c provided by the present embodiment comprises a plurality of $1^{st}$ stage processors 322-2~322-m, a combinator 324 and a $2^{nd}$ stage processor 326. Each of the $1^{st}$ stage processor 322-1~322-m performs $1^{st}$ stage DNN processing for one of the sensing data D1~Dm respectively and generates a $1^{st}$ stage learning result Out_b1~Out_bm. The combinator 324 couples with the $1^{st}$ stage processors 322-1~322-m, so as to combine the $1^{st}$ stage learning result Out_b1~Out_bm into a combination data D_Com. In addition, the combinator 324 further couples with the $2^{nd}$ stage processor 326. And the $2^{nd}$ stage processor 326 performs $2^{nd}$ stage DNN processing for the combination data D_Com and obtains the analysis result Out_Final.

Figure 4:
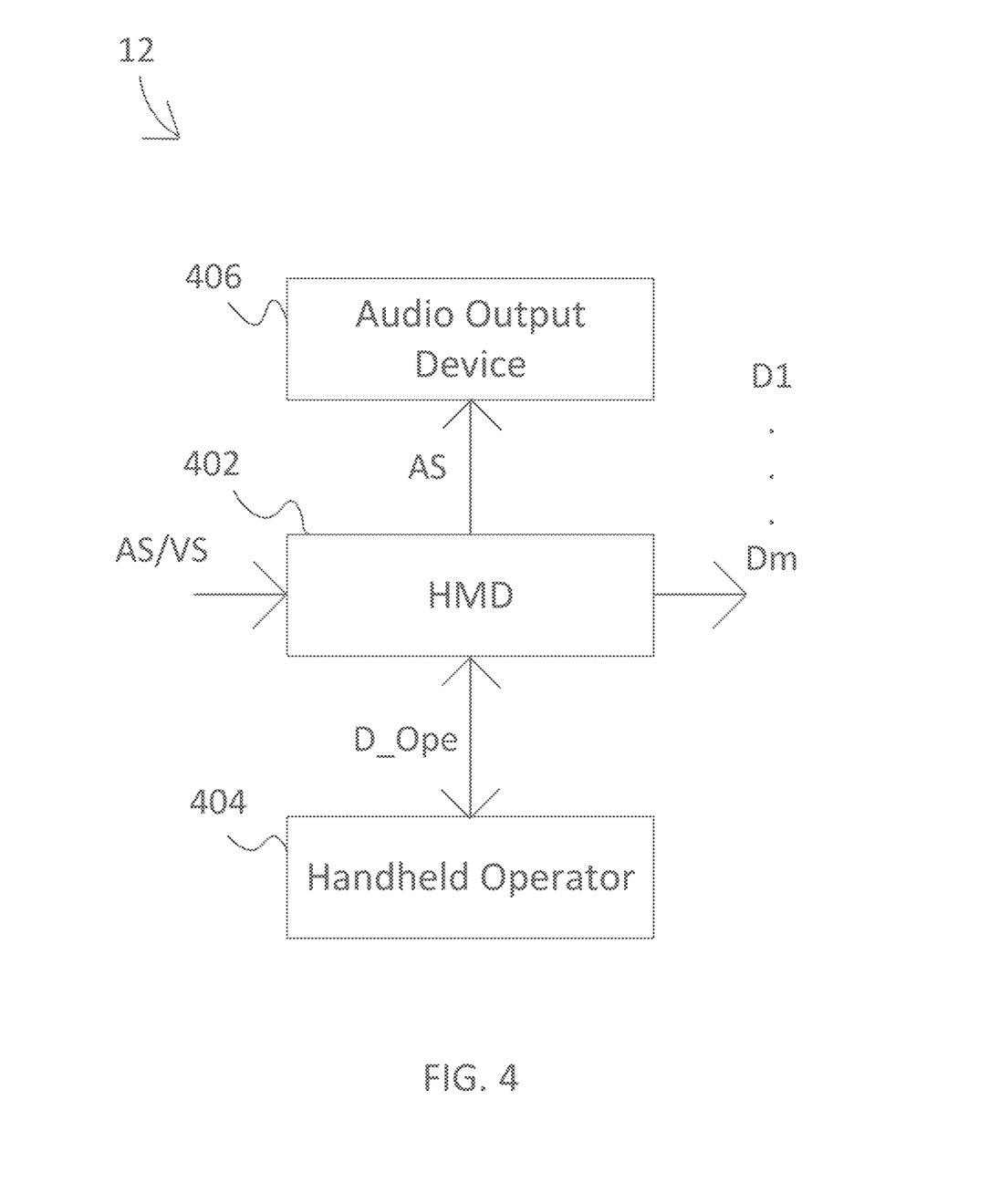
FIG. 4 is shown as a block diagram of the immersive module according to one embodiment of the present disclosure.
Figure 5A:
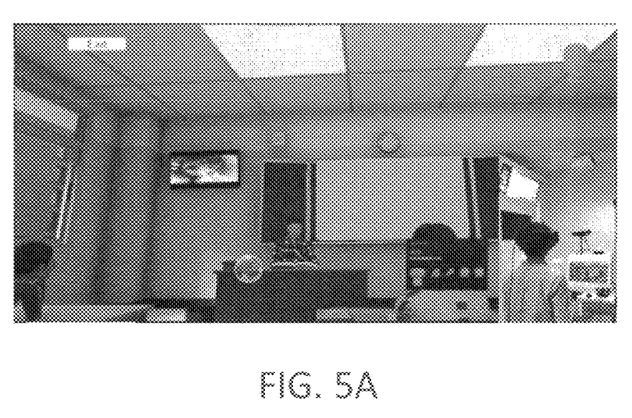
FIG. 5A is shown as a diagram of 3D scenes environment of a virtual classroom.

FIG. 4 is shown as a block diagram of the immersive module according to one embodiment of the present disclosure. Please referring to FIG. 4, the immersive module 12 provided by the present embodiment is capable for receiving the test video VS and/or test audio AS from the host device 16 or 18, and providing the immersive experience for the test-receiver, such like a virtual reality environment. In the present embodiment, the immersive module 12 comprises a head mounted display (HMD) 402, which is able to display the received test video VS to the test-receiver. For example, FIG. 5A shows a 3D scenes environment of a virtual classroom.

In some embodiments, the immersive module 12 further comprises handheld controller 404, which is able to couple with HMD 402 through wireless matter, such like Bluetooth, ZigBee, RFID or other wireless communication protocol, or wire matter, such like USB 2.0, 3.0, Type-C, Lighting, or other connection port. Of course, in other embodiments, the handheld controller 404 is able to sense the gestures and/or operation of test-receiver and output the operation sensing data D_Ope. If the handheld controller 402 couples with the HMD 402, the operation sensing data D_Ope can be transmitted to the HMD 402. Then, the HMD 402 outputs the operation sensing data D_Ope as one of the sensing data D1~Dm.

Figure 5B:
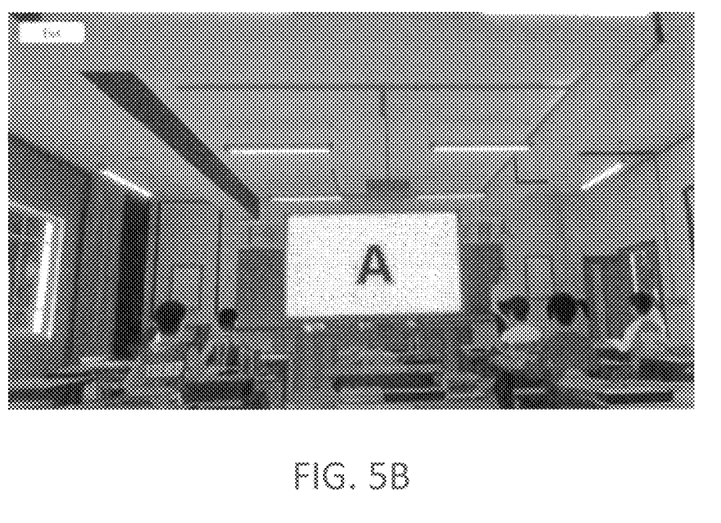
FIG. 5B is shown as a diagram of the scenes of continuous performance test.
Figure 5C:
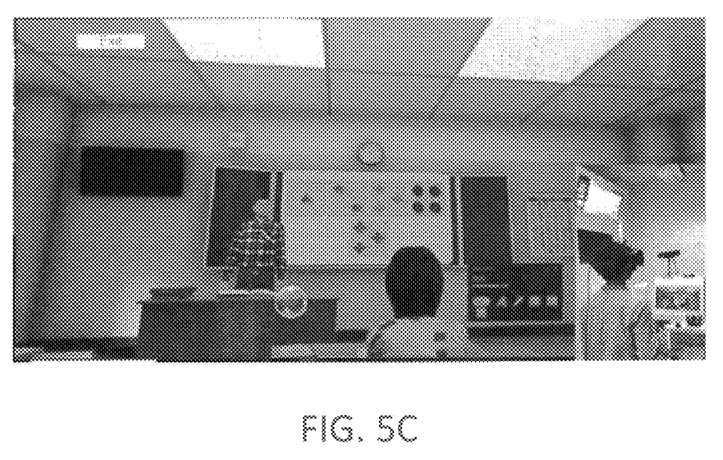
FIG. 5C is shown as a diagram of the scenes of Wisconsin card sorting test.

Please refer to the FIG. 4 continually, in this embodiment, the test video VS comprises continuous performance test, such like the scenes shown in the FIG. 5B, and Wisconsin card sorting test, such like the scenes shown in the FIG. 5C. In the scenes of continuous performance test shown in FIG. 5B, it provides a visual task. In each round of task, a serial of different alphabets would be displayed on the black board in the scenes. When the showing order of the alphabets is conformed as a specific order, for example, "X" is shown after "A", the test-receiver need perform a specific operation, such like pressing a specific button on the handheld controller 404; otherwise, the test-receiver should not press the specific button. When the test-receiver presses the specific button, the handheld 404 would output a corresponding operation sensing data D_Ope to the HMD 402.

In addition, the Wisconsin card sorting test shown in FIG. 5C is set by stimulus cards and response cards saved in the question base. Each of cards has different assemble of numbers, colors and shapes. The test-receiver need operate the handheld controller 404 to arrange the response cards according to the order of numbers, colors and shapes designated by the test-provider. When the test-receiver arrange the stimulus cards and response cards through the handheld controller 404, it would generate the operation sensing data D_Ope.

Please refer the FIG. 4 again, the immersive module 12 further comprises audio output device 406, such like earphone. The audio output device 406 is able to couple with HMD 402 through wireless matter, such like Bluetooth, ZigBee, RFID or other wireless communication protocol, or wire matter, such like USB 2.0, 3.0, Type-C, lighting, audio port, HDMI, Mini HDMI, or other type of multi-media communication wire. Of course, the audio output device 406 can be selectively coupled with the host device 16 or 18. If the audio output device 406 is coupled to the HMD 402, it would transmit the test audio AS to the audio output device 406 as receiving test audio AS, such that the test audio AS would be provided to the test-receiver through the audio output device 406.

Figure 6:
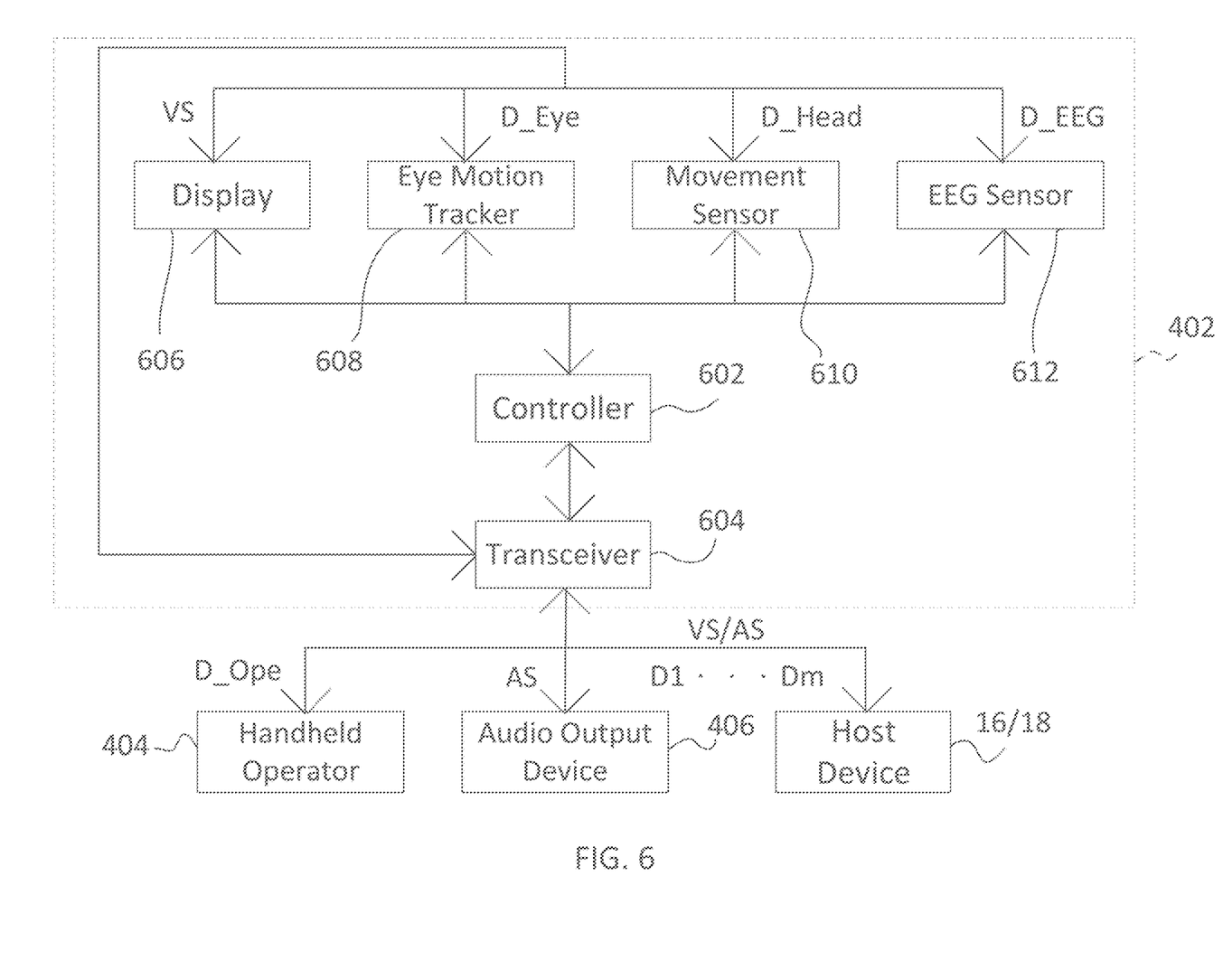
FIG. 6 is shown as a block diagram of the HMD according to one embodiment of the present disclosure.

FIG. 6 is shown as a block diagram of the HMD according to one embodiment of the present disclosure. Please referring to the FIG. 6, the HMD 402 comprises a controller 602, such like a processor, a micro controller, a single chip, etc. In addition, the HMD 402 further comprises at least one transceiver 604 and a display 606, which are able to couple with the controller 602. The transceiver 604 can couple with the handheld controller 404, audio output device 406, and host device 16 or 18 via the aforementioned wire or wireless matter. The display 606 may be a LCD, OLED, or micro LED display. In other selective embodiments, the display 606 may a external display device, such like mobile phone. When the transceiver 604 receives the test video VS, the controller 602 controls the display 606 showing the test video VS to the test-receiver, such as showing the scenes in the FIGS. 5A, 5B and 5C.

In other embodiments, the HMD 402 further comprises eye motion tracker 608 and movement sensor 610, which are coupled with controller 602 as well. The eye motion tracker 608 is capable for sensing the movement of the test-receiver's eyeball, and generating the eye motion sensing data D_Eye. The movement sensor 616 is capable for sensing the movement of the test-receiver's head and generating the movement sensing data D_Head. The controller 602 is able to control transceiver 604 output the eye sensing data D_Eye and head movement sensing data D_Head to the host device 16 and 18 as parts of the sensing data D1~Dm, so as to perform analysis.

In other embodiments, the HMD 402 further comprises an EEG sensor 612, which is able to couple with the controller 602. The EEG sensor 612 is capable for sensing the variation of test-receiver's brainwave and generating EEG sensing data D_EEG. Similarly, the controller 602 is able to control the transceiver 604 output the EEG sensing data D_EEG as one of the sensing data D1~Dm to the host device 16 or 18 to perform analysis.

The aforementioned HMD 402 is able to provide different interference events, and output corresponding sensing data according to the test-receiver's response. For example, the controller 602 is able to control the audio output device 406 output the test audio AS, such like the noise, broadcast, whistling of ambulance from outside of classroom, as the display 606 showing the test video VS. Meanwhile, in accordance with the test-receiver's response, the eye motion tracker 608, movement sensor 610 and EEG sensor 612 are able to generate the eye motion sensing data D_Eye, head movement sensing data D_Head and EEG sensing data D_EEG.

Figure 7:
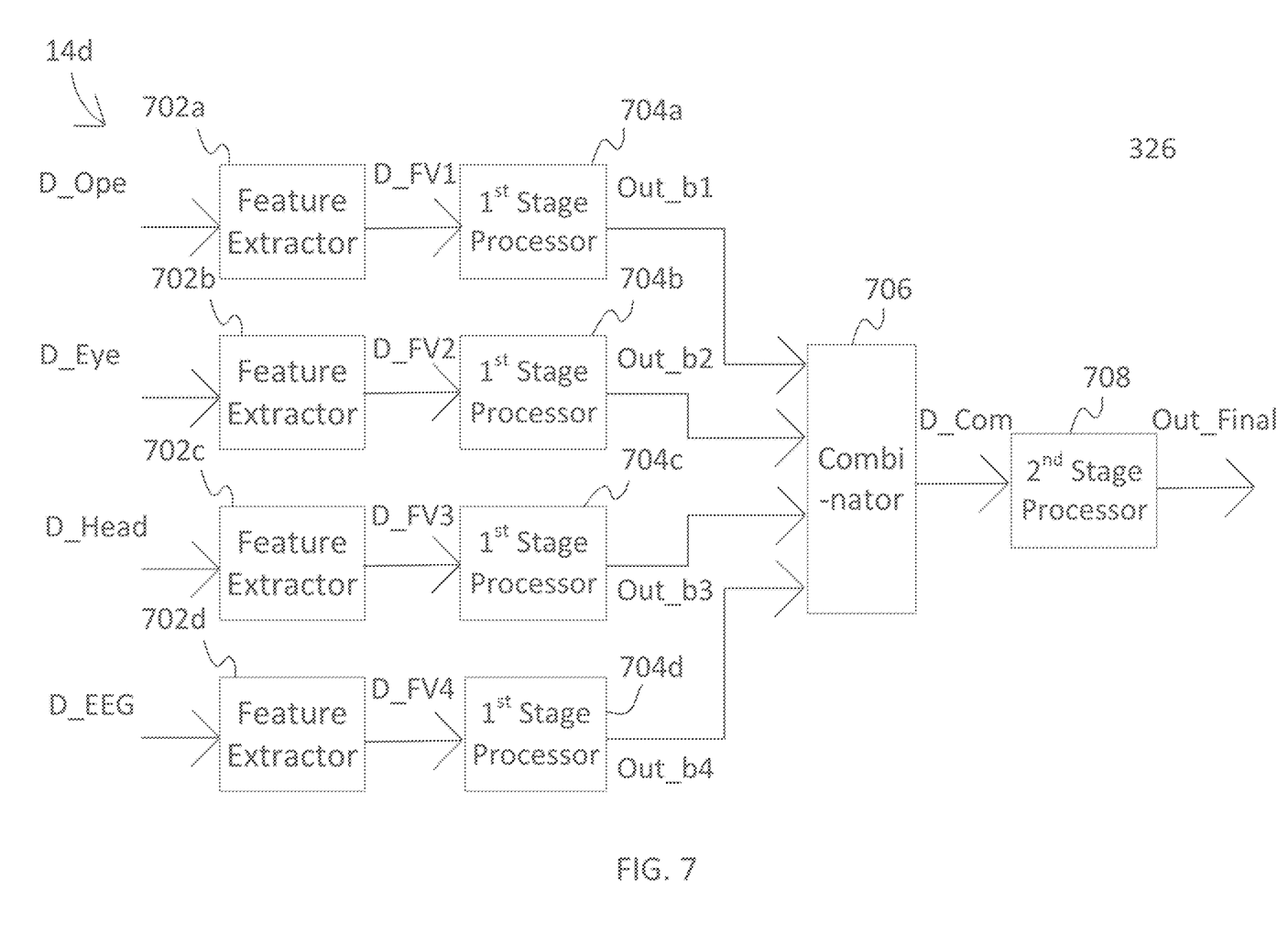
FIG. 7 is shown as a block diagram of the analysis module according to the embodiment in the FIG. 6.

FIG. 7 is shown as a block diagram of the analysis module according to the embodiment in the FIG. 6. Please referring to FIG. 7, the analysis module 14d in this embodiment comprises a plurality of feature extractors 702a~702d, a plurality of $1^{st}$ stage processor 704a~704d, a combinator 706, and a $2^{nd}$ stage processor 708. The feature extractors 702a~702d are configure for receiving a plurality of sensing data. In the present embodiment, those sensing data are operation sensing data D_Ope, eye motion sensing data D_Eye, head movement sensing data D_Head and EEG sensing data D_EEG. Each of feature extractors is capable for extracting a plurality feature values from one of received sensing data respectively, so as to obtain a plurality of feature data D_FV1~D_FV4. The one who skilled in this art should know that the feature extractors 702a~702d may be configured in any of analysis modules in aforementioned embodiments disclosed by the FIGS. 3A to 3C, so as to pre-process the sensing data D1~Dm.

Each of $1^{st}$ stage processors 704a~704d couples with one of feature extractors 702a~702d, so as to perform $1^{st}$ stage DNN process for the feature data D_FV1~D_FV4, and generate the $1^{st}$ stage learning results Out_b1~Out_b4. Those $1^{st}$ stage processor 704a~704d further couple with combinator 146. Accordingly, the combinator 146 combines the $1^{st}$ stage learning result Out_b1~Out_b4 into a combination data D_Com. In addition, the combinator 706 is further coupled with the $2^{nd}$ stage processor 708, and the $2^{nd}$ stage processor 708 performs the $2^{nd}$ stage DNN process for the combination data D_Com and obtains the analysis result Out_Final, which is shown whether the test-receiver has the tendency on ADHD.

In some embodiments, the $1^{st}$ stage processor 704a~704d have been trained. Therefore, the processing effect of the analysis module 14d can be raised.

Figure 8:
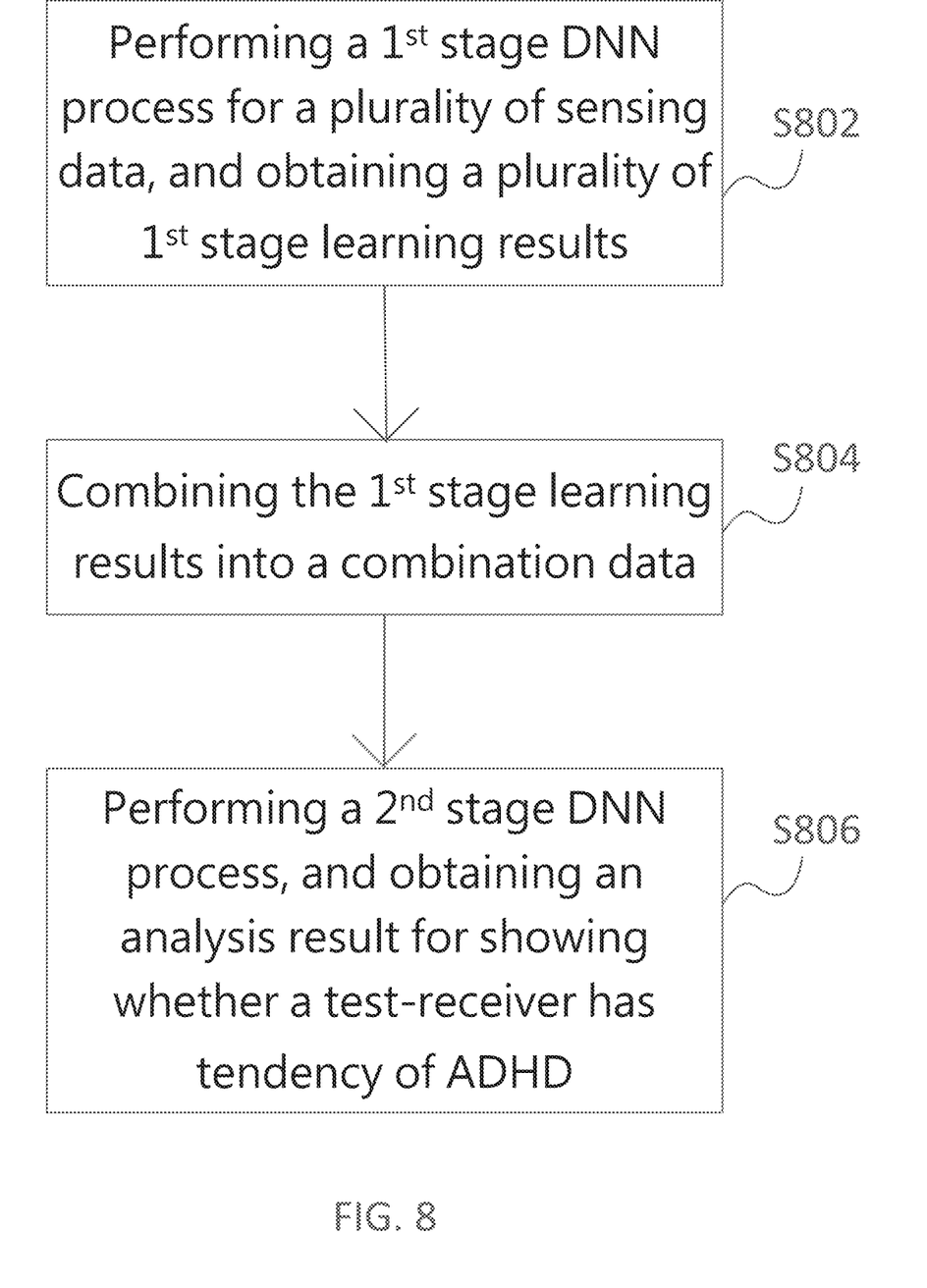
FIG. 8 is shown as a flow chart of the analysis method for ADHD according to one embodiment of the present disclosure.

FIG. 8 is shown as a flow chart of the analysis method for ADHD according to one embodiment of the present disclosure. Please referring to FIG. 8, the analysis method provided by the present embodiment comprises performing $1^{st}$ stage DNN process for a plurality of sensing data, so as to obtain a plurality of $1^{st}$ stage learning results as the description in the step S802. Then, the $1^{st}$ stage learning results are combined into a combination data as the description in the step S804. Finally, the combination data is performed $2^{nd}$ stage DNN process, so as to obtain a analysis result for showing whether the test-receiver has the tendency on ADHD as the description in the step S806.

In some embodiment, the step S802 further comprises pre-extracting a plurality of feature value to obtain a plurality of feature data, and performing $1^{st}$ stage DNN process for those feature data.

In summary, the present disclosure has at least characteristics as following.
1. Since the present disclosure adopts the immersive module providing the test video and/or test audio to the test-receiver, so as to create the immersive experience for the test-receiver. Therefore, the disclosure is capable for avoiding the limitation of the location and environment.
2. Since the present disclosure performs DNN process for the sensing data from the test-receiver to determine whether the test-receiver has the tendency of ADHD, the mistake of the test-provider's subjective judgment can be avoided.
3. In the present disclosure, it adopts $1^{st}$ stage DNN process and $2^{nd}$ stage DNN process, such that it has higher accuracy.
4. Since the $1^{st}$ stage DNN processor can be had trained, the processing effect is higher as well.

While the present disclosure has been described by means of specific embodiments, numerous modifications and variations could be made thereto by those skilled in the art without departing from the scope and spirit of the present disclosure set forth in the claims.

What is claimed is:

1. An analysis apparatus for ADHD, suitable for receiving a plurality of sensing data from a test-receiver, comprising:
   a plurality of $1^{st}$ stage processor, configured for performing $1^{st}$ stage process for the sensing data respectively, and outputting a plurality of $1^{st}$ stage learning results;
   a combinator, coupled with the $1^{st}$ stage processor, for combining the $1^{st}$ stage learning results into a combination data; and
   a $2^{nd}$ stage processor, coupled with the combination, for performing $2^{nd}$ DNN process for the combination data and outputting an analysis result.

2. The analysis apparatus of claim 1, further comprising:
   a plurality of feature extractors, configured for receiving the sensing data to obtain a plurality of feature values, wherein each of feature extractors is coupled to one of the $1^{st}$ stage processor respectively, so as to perform $1^{st}$ DNN process for the feature values.

3. The analysis apparatus of claim 1, wherein the sensing data comprises a test-receiver's EEG sensing data, eye motion sensing data, and at least one movement sensing data.

4. A diagnostic system for ADHD, comprising:
   an immersive module, configured for providing at least one of a test video and a test audio to a test-receiver, and sensing the test-receiver's response for the test video and/or test audio, so as to output a plurality of sensing data; and
   an analysis module, coupled with the immersive module via wire or wireless matter, so as to receive the sensing data, wherein the analysis module comprises:
      a plurality of $1^{st}$ stage processor, configured for performing $1^{st}$ stage process for the sensing data respectively, and outputting a plurality of $1^{st}$ stage learning results;
      a combinator, coupled with the $1^{st}$ stage processor, for combining the $1^{st}$ stage learning results into a combination data; and
      a $2^{nd}$ stage processor, coupled with the combination, for performing $2^{nd}$ DNN process for the combination data and outputting an analysis result.

5. The diagnostic system of claim 4, wherein the analysis module further comprises:
a plurality of feature extractors, configured for receiving the sensing data to obtain a plurality of feature values, wherein each of feature extractors is coupled to one of the $1^{st}$ stage processor respectively, so as to perform $1^{st}$ DNN process for the feature values.

6. The diagnostic system of claim 4, wherein the immersive module comprises:
a head mounted display (HMD), configured for displaying the test video, and sensing the test-receiver's response to output at least one of the sensing data.

7. The diagnostic system of claim 6, wherein the HMD further comprises:
a controller;
a display, coupled to the controller;
an eye motion tracker, coupled to the controller and configured for sensing the motion of the test-receiver's eyeball to output an eye motion sensing data;
a movement sensor, coupled to the controller and configured for sensing the movement of the test-receiver's head to output a head movement sensing data; and
a transceiver, coupled to the controller,
wherein when the transceiver receives the test video, the controller controls the display displaying the test video, and
the controller controls the transceiver transmitting the eye motion sensing data and the head movement sensing data to the analysis module as at least part of the sensing data.

8. The diagnostic system of claim 7, wherein the HMD further comprises:
an EEG sensor, coupled to the controller and configured for sensing the test-receiver's brainwave to output an EEG sensing data,
wherein when the EEG sensor outputs the EEG sensing data, the controller controls the transceiver transmitting the EEG sensing data to the analysis module as at least part of the sensing data.

9. The diagnostic system of claim 7, wherein the HMD further comprises:
at least one handheld operator, coupled with the transceiver via wire or wireless matter, and configured for sensing the test-receiver's gesture and/or operation on the handheld operation to output an operation sensing data,
when the operation sensing data is transmitted to the transceiver by the handheld operation, and the controller controls the transceiver transmitting the operation sensing data to the analysis module as at least part of the sensing data.

10. The diagnostic system of claim 7, further comprising:
a first host device, coupled with the transceiver via wire or wireless matter; and
a second host device, coupled with the first host device via wire or wireless matter, wherein the analysis module is installed on the second host device,
wherein the first host device transmits the test video and/or test audio to the transceiver, and transmits the sensing data to analysis module installed on the second host device from the transceiver to analyze.

11. The diagnostic system of claim 7, further comprising:
a host device, coupled to the transceiver via wire or wireless matter, wherein the analysis module is installed on the host device,
wherein the host device transmits the test video and/or test audio to the transceiver, and receiving the sensing data from the transceiver, so as to make the analysis module to analyze the sensing data.

12. The diagnostic system of claim 6, wherein the immersive module comprises:
a audio output device, configured for outputting the test audio to the test-receiver.

13. An analysis method for ADHD, comprising the following steps:
performing a $1^{st}$ stage DNN process for a plurality of sensing data, and obtaining a plurality of $1^{st}$ stage learning results;
combining the $1^{st}$ stage learning results into a combination data; and
performing a $2^{nd}$ stage DNN process, and obtaining an analysis result for showing whether a test-receiver has tendency of ADHD.

14. The analysis method of claim 13, wherein the step of performing the $1^{st}$ stage DNN process comprises the following steps:
extracting a plurality of feature values from the sensing data; and
performing the $1^{st}$ stage DNN process for the feature values to obtain the $1^{st}$ stage learning results,
wherein the sensing data involves the test-receiver's EEG sensing data, eye motion sensing data and at least one movement sensing data.

* * * * *